US 10,258,483 B2

(12) United States Patent
Black et al.

(10) Patent No.: US 10,258,483 B2
(45) Date of Patent: Apr. 16, 2019

(54) LAMINATE IMPLANTABLE MEDICAL DEVICES

(71) Applicant: DeGen Medical, Inc., Florence, SC (US)

(72) Inventors: Craig Black, Florence, SC (US); Kidong Yu, Florence, SC (US)

(73) Assignee: DeGen Medical, Inc., Florence, SC (US)

( * ) Notice: Subject to any disclaimer, the term of this patent is extended or adjusted under 35 U.S.C. 154(b) by 124 days.

(21) Appl. No.: 15/241,855

(22) Filed: Aug. 19, 2016

(65) Prior Publication Data

US 2018/0049886 A1   Feb. 22, 2018

(51) Int. Cl.
*A61F 2/44*      (2006.01)
*A61F 2/30*      (2006.01)

(52) U.S. Cl.
CPC ............ *A61F 2/447* (2013.01); *A61F 2/4455* (2013.01); *A61F 2002/30131* (2013.01); *A61F 2002/30331* (2013.01); *A61F 2002/30476* (2013.01); *A61F 2002/30485* (2013.01); *A61F 2002/30593* (2013.01); *A61F 2002/30971* (2013.01); *A61F 2002/4475* (2013.01); *A61F 2240/001* (2013.01)

(58) Field of Classification Search
CPC .............................................. A61F 2/44–2/447
USPC .......................................... 623/17.11–17.16
See application file for complete search history.

(56) References Cited

U.S. PATENT DOCUMENTS

| | | |
|---|---|---|
| 5,961,554 A | 10/1999 | Janson et al. |
| 5,980,572 A | 11/1999 | Kim et al. |
| 6,102,950 A | 8/2000 | Vaccaro |
| 6,558,424 B2 | 5/2003 | Thalgott |
| 6,743,257 B2 | 6/2004 | Castro |
| 6,761,739 B2 | 7/2004 | Shepard |
| 7,037,339 B2 | 5/2006 | Houfburg |
| 7,137,997 B2 | 11/2006 | Paul |
| 7,220,280 B2 | 5/2007 | Kast et al. |
| 7,396,365 B2 | 7/2008 | Michelson |
| D629,104 S | 12/2010 | Calverley et al. |
| 7,875,080 B2 | 1/2011 | Puno et al. |
| 8,025,680 B2 | 9/2011 | Hayes et al. |
| 8,114,092 B2 | 2/2012 | Altarac et al. |

(Continued)

FOREIGN PATENT DOCUMENTS

| | | |
|---|---|---|
| CN | 101049254 | 5/2010 |
| WO | WO2014028635 | 2/2014 |

OTHER PUBLICATIONS

Aesculap Implant Systems, "CeSpaceXP Interbody System," p. 1, [retrieved on Apr. 24, 2014]. Retrieved from the Internet: <URL: http://www.aesculapimplantsystems.com/default.aspx?pageid=3945>.

(Continued)

*Primary Examiner* — Nicholas J Plionis
(74) *Attorney, Agent, or Firm* — Buchanan Van Tuinen LLC

(57) ABSTRACT

Implantable medical devices suitable for implantation in spaces between bones, such as in the spaces between vertebrae in a vertebral column of an animal, are described. An implantable medical device comprises a laminate structure in which a cover conforms to and is attached to a main body. The implantable medical device is suitable for implantation in spaces between bones, such as in the spaces between vertebrae in a vertebral column of an animal.

6 Claims, 8 Drawing Sheets

(56) References Cited

U.S. PATENT DOCUMENTS

| | | | |
|---|---|---|---|
| 8,303,879 | B2 | 11/2012 | Bertele et al. |
| 8,328,872 | B2 | 12/2012 | Duffield et al. |
| 8,394,145 | B2 | 3/2013 | Weiman |
| 8,425,604 | B2 | 4/2013 | Trieu |
| D682,427 | S | 5/2013 | Farris et al. |
| 8,496,706 | B2 | 7/2013 | Ragab et al. |
| 8,496,713 | B2 | 7/2013 | Bennett et al. |
| 8,506,629 | B2 | 8/2013 | Weiland |
| 8,518,120 | B2 | 8/2013 | Glerum et al. |
| 8,523,910 | B2 | 9/2013 | Seifert et al. |
| 8,545,566 | B2 | 10/2013 | Niemiec et al. |
| 8,551,176 | B2 | 10/2013 | Ullrich, Jr. et al. |
| 8,556,974 | B2 | 10/2013 | Suh et al. |
| 8,556,979 | B2 | 10/2013 | Glerum et al. |
| 8,597,355 | B2 | 12/2013 | Hansell |
| 8,597,359 | B2 | 12/2013 | Butler |
| 8,617,244 | B2 | 12/2013 | Reichen et al. |
| 8,632,593 | B2 | 1/2014 | Suh et al. |
| 8,641,768 | B2 | 2/2014 | Duffield et al. |
| 8,900,309 | B2 | 12/2014 | James et al. |
| 9,216,096 | B2 | 12/2015 | Lynn et al. |
| 2003/0004576 | A1* | 1/2003 | Thalgott ............... A61F 2/4455 623/17.16 |
| 2004/0102850 | A1 | 5/2004 | Shepard |
| 2005/0149192 | A1 | 7/2005 | Zucherman et al. |
| 2007/0032871 | A1 | 2/2007 | Michelson |
| 2007/0073400 | A1 | 3/2007 | Paul |
| 2007/0270968 | A1* | 11/2007 | Baynham ............... A61F 2/447 623/17.11 |
| 2007/0293948 | A1 | 12/2007 | Bagga et al. |
| 2008/0306596 | A1* | 12/2008 | Jones ................... A61F 2/4455 623/17.16 |
| 2009/0076616 | A1 | 3/2009 | Duggal et al. |
| 2009/0099659 | A1* | 4/2009 | Oh ....................... A61F 2/4455 623/17.16 |
| 2009/0171461 | A1 | 7/2009 | Conner et al. |
| 2009/0198278 | A1 | 8/2009 | Shibata et al. |
| 2010/0305704 | A1* | 12/2010 | Messerli ............... A61F 2/442 623/17.16 |
| 2011/0040384 | A1 | 2/2011 | Junn et al. |
| 2011/0160860 | A1 | 6/2011 | Johnston et al. |
| 2011/0172769 | A1 | 7/2011 | Ganem et al. |
| 2011/0172774 | A1 | 7/2011 | Varela |
| 2011/0184522 | A1 | 7/2011 | Melkent et al. |
| 2011/0190888 | A1 | 8/2011 | Bertele et al. |
| 2011/0224796 | A1 | 9/2011 | Weiland et al. |
| 2011/0307016 | A1 | 12/2011 | Reglos et al. |
| 2012/0078370 | A1 | 3/2012 | James et al. |
| 2012/0089191 | A1 | 4/2012 | Altarac et al. |
| 2012/0136443 | A1 | 5/2012 | Wenzel |
| 2012/0316649 | A1 | 12/2012 | Johnston et al. |
| 2013/0030544 | A1 | 1/2013 | Studer |
| 2013/0060336 | A1* | 3/2013 | Hooper ................. A61F 2/447 623/17.11 |
| 2013/0060339 | A1 | 3/2013 | Duffield et al. |
| 2013/0131726 | A1 | 5/2013 | Suh et al. |
| 2013/0144388 | A1 | 6/2013 | Emery et al. |
| 2013/0158667 | A1 | 6/2013 | Tabor et al. |
| 2014/0012382 | A1 | 1/2014 | Doty |
| 2014/0277474 | A1 | 9/2014 | Robinson et al. |
| 2014/0277508 | A1* | 9/2014 | Baynham ............... A61F 2/447 623/17.16 |
| 2015/0100129 | A1 | 4/2015 | Waugh et al. |
| 2015/0282941 | A1 | 10/2015 | Chokshi |

OTHER PUBLICATIONS

Synthes Spine, "Advanced ACF Spacer: An allograft spacer with demineralized surfaces for anterior cervical interbody fusion," Synthes. com, 2004, pp. 1-7.

Lemke, Johannes, et al., "Polyetheretherketone (PEEK) Spacers for Anterior Cervical Fusion: A Retrospective Comparative Effectiveness Clinical Trial," Open Orthop. J. 2011; 5: 348-353.

Bonovo Orthopedics, "NuVasive PCM Cervical Disc," pp. 1-4, accessed Feb. 26, 2014, http://www.bonovo-ortho.com/Products/Spine(Cervical).php.

Depuy Spine, "Surgical Technique: VG2 Cervical Allograft," Brochure from Depuy Spine, Virginia Beach, VA, 2003.

Globus Medical, "Sustain & Sustain-R, Large, Trapezoidal thoracolumbar vertebral body replacement device," pp. 1-3, accessed Feb. 26, 2014, http://www.globusmedical.com/portfolio/sustain-sustain-r-large/.

Globus Medical, "Colonial, cervical interbody fusion device," pp. 1-2, accessed Feb. 26, 2014, http://globusmedical.com/portfolio/colonial/.

*Globus Medical Inc. V. Depuy Synthes Products, LLC, Depuy Synthes Sales, Inc.*, Complaint, Case No. 1:13-cv-00854-UNA, at pp. 1-5 (D. Del. May 15, 2013).

Ho, Cheng, et al., "Kurokawa-type Laminoplasty using Hydroxyapatite Spacer for Cervical Myelopathy," Hong Kong J. Orthop. Surg. 2004: 8 (1):12-21.

Mahe Medical, "Perfect Spine, Vertebral Spacer System," from www.slideshare.net, slide No. 10, accessed Feb. 26, 2014, http://image.slidesharecdn.com/cages-130721071738-phpapp02/95/slide-10-638.jpg?cb=1374409152.

Niu, Chi-Chien et al., "Trapezoidal Titanium Cage in Anterior Cervical Interbody Fusion: A Clinical Experience," Chang Gung Med. J. Apr. 2005; 28 (4): 212-221.

Nutech Medical, "Interbody," Nutchmedical.com, pp. 1-3, accessed Feb. 26, 2014, http://nutechmedical.com/products/spine/interbody/.

United States Patent and Trademark Office, Office Action for U.S. Appl. No. 86/253,948, Applicant: DeGen Medical, Inc., dated Dec. 29, 2014, pp. 33, 39, 42, 53 and 54.

Gelisim Medical, "Spinal Cerrahi", Gelisimmedikal.com, pp. 1-2, 2013, accessed Jun. 27, 2014, http://www.gelisimmedikal.com/eng/servical-peek-cage.asp.

European Patent Office, Extended European Search Report for Application No. 15162843.5, dated Jul. 5, 2016, p. 1-6.

* cited by examiner

LAMINATE IMPLANTABLE MEDICAL DEVICES

FIELD

The disclosure relates generally to the field of implantable medical devices. More particularly, the disclosure relates to implantable medical devices suitable for implantation in spaces between bones, such as in the spaces between vertebrae in a vertebral column of an animal.

BACKGROUND

Over time, bone may degenerate as a result of trauma, disease, and natural processes, such as aging. Bone degeneration can affect surrounding tissues and have a significant negative impact on the lifestyle of an animal. For example, destabilization of a spine in a vertebrate, such as a human being, may result in alteration of the spacing between adjacent vertebrae. This can place pressure on nerves that pass between the vertebral bodies. In turn, this pressure can cause pain, discomfort, and, eventually, nerve damage.

One way to alleviate the pain and discomfort that occurs after the degeneration or destabilization of a portion of the spine is to implant a medical device into the space between two adjacent vertebrae. Implanted in this manner, the medical device supports the structure of the spine by maintaining a desired spacing between the adjacent vertebrae. The medical device can facilitate the fusion of the adjacent vertebrae, too.

One challenge in designing implantable medical devices intended for placement between vertebrae is developing a structure that can be readily positioned while also providing the desired functionality and capabilities.

While the art provides several examples of implantable medical devices suitable for implantation in spaces between bones, such as in the spaces between vertebrae in a vertebral column of an animal, a need for improved implantable medical devices remains.

BRIEF SUMMARY OF SELECTED EXAMPLES

Various example implantable medical devices are described and illustrated herein.

An example implantable medical device comprises a main body defining an upper surface, a lower surface, a proximal surface, a distal surface, a first lateral surface, and a second lateral surface, the proximal surface defining first and second lateral ribs and a channel bounded by the first and second lateral ribs; and a cover attached to the main body, the cover comprising an upper portion, a lower portion, and a strut extending between and connecting the upper and lower portions, the strut disposed within the channel of the main body.

Another example implantable medical device comprises a main body defining an upper surface, a lower surface, a proximal surface, a distal surface, a first lateral surface, and a second lateral surface, the upper surface defining an upper main body opening, the lower surface defining a lower main body opening, and the proximal surface forming a rounded nose and defining first and second lateral ribs and a channel bounded by the first and second lateral ribs; the main body defining a plurality of cavities; and the main body having an inner circumferential wall defining a passageway extending through the main body from the upper main body opening to the lower main body opening; and a cover attached to the main body, the cover comprising an upper portion defining an upper cover opening, a lower portion defining a lower cover opening, and a strut extending between and connecting the upper and lower portions, the strut disposed within the channel of the main body, the cover defining a plurality of tabs, each tab of the plurality of tabs disposed within a cavity of the plurality of cavities; wherein the upper cover opening has substantially the same size and configuration of the upper main body opening; and wherein the lower cover opening has substantially the same size and configuration of the lower main body opening.

Another example implantable medical device comprises a radiolucent main body defining an upper surface, a lower surface, a proximal surface, a distal surface, a first lateral surface, and a second lateral surface, the upper surface defining an upper main body opening, the lower surface defining a lower main body opening, and the proximal surface forming a rounded nose and defining first and second lateral ribs and a channel bounded by the first and second lateral ribs; the distal surface of the main body at least partially defining a first plurality of cavities; the first lateral surface of the main body at least partially defining a second plurality of cavities; and the main body having an inner circumferential wall defining a passageway extending through the main body from the upper main body opening to the lower main body opening; and a radiopaque cover attached to the main body, the cover comprising an upper portion defining an upper cover opening, a lower portion defining a lower cover opening, and a strut extending between and connecting the upper and lower portions, the strut disposed within the channel of the main body, the cover defining a first plurality of tabs, each tab of the first plurality of tabs disposed within a cavity of the first plurality of cavities; and the cover defining a second plurality of tabs, each tab of the second plurality of tabs disposed within a cavity of the second plurality of cavities; wherein the upper cover opening has substantially the same size and configuration of the upper main body opening; and wherein the lower cover opening has substantially the same size and configuration of the lower main body opening.

Various methods of manufacturing implantable medical devices are also described and illustrated herein.

An example method of manufacturing implantable medical devices comprises selecting sheet stock; surface treating the selected sheet stock; forming the a flat pattern in the sheet stock; selecting a main body; conforming the flat pattern to the main body; and attaching the flat pattern to the main body as a cover to produce an implantable medical device.

Additional understanding of the inventive implantable medical devices and methods can be obtained by reviewing the detailed description of selected examples, below, with reference to the appended drawings.

DETAILED DESCRIPTION OF SELECTED EXAMPLES

The following detailed description and the appended drawings describe and illustrate various example apparatuses and methods. The description and drawings are provided to enable one skilled in the art to make, use and/or perform examples of the inventive apparatuses and methods. They are not intended to limit the scope of the claims in any manner.

The implantable medical devices described herein are useful in the maintaining of support between bones of an animal, such as within the vertebral column of an animal. For example, the implantable medical devices described herein are suitable for use implantation within various intervertebral spaces along a vertebral column of a human to assist in the maintaining of a desired spacing between adjacent vertebrae. The example implantable medical devices are sized and configured for implantation between adjacent vertebrae of a human.

Figure 8:
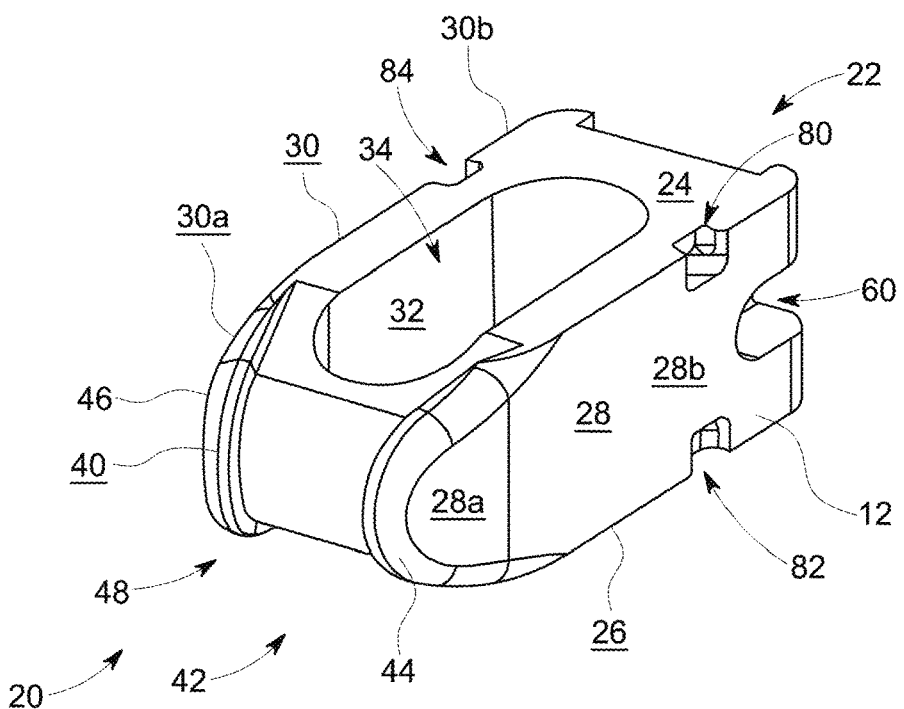
FIG. 8 is a perspective view of the main body component of the first example implantable medical device.
Figure 9:
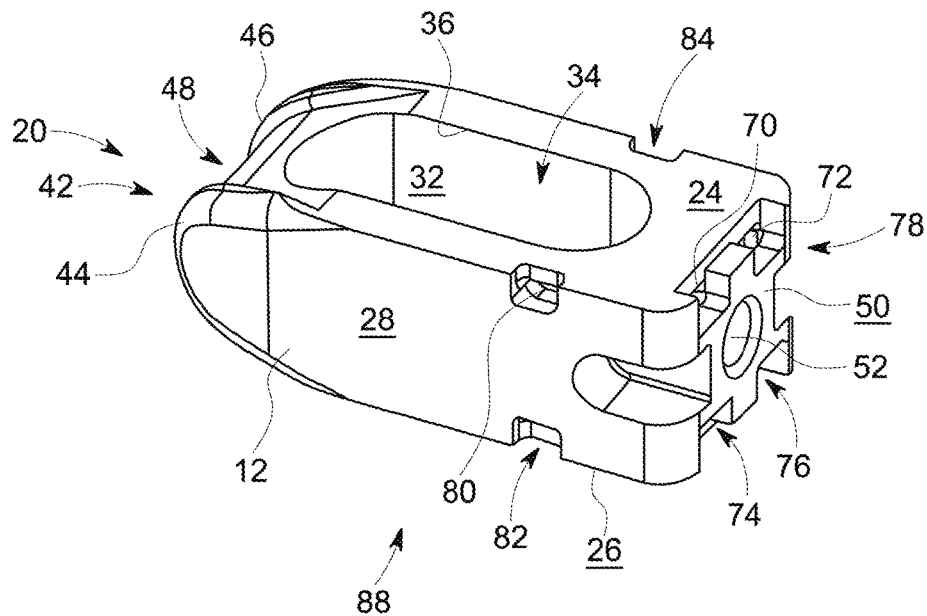
FIG. 9 is another perspective view of the main body component of the first example implantable medical device.
Figure 11:
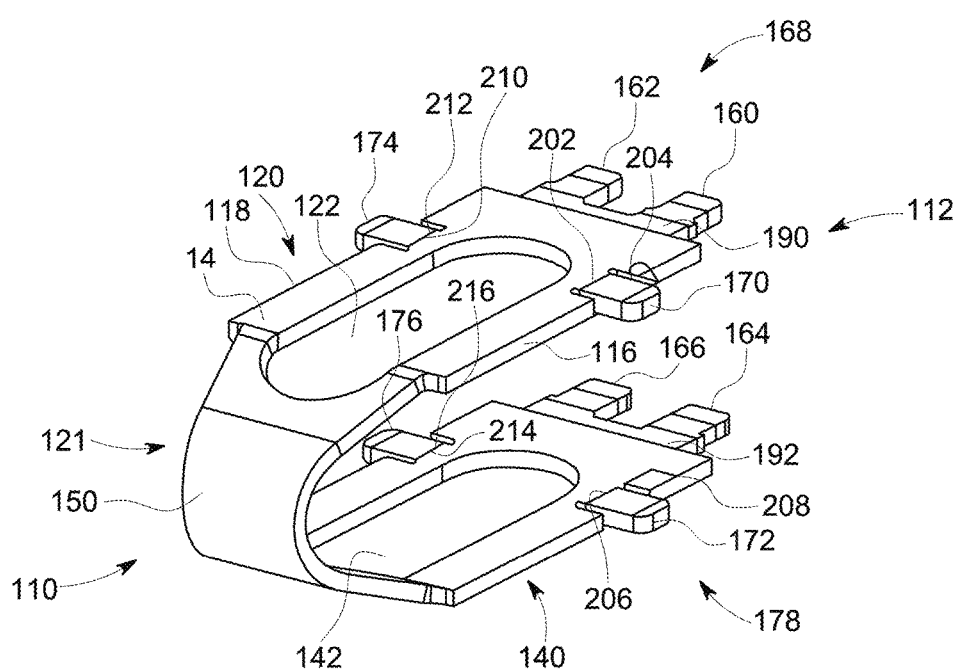
FIG. 11 is a perspective view of the cover component of the first example implantable medical device.

FIGS. 1, 2, 3, 4, 5, 6, and 7 illustrate an example implantable medical device 10. The implantable medical device 10 comprises a main body 12 and a cover 14. The implantable medical device 10 is a laminate structure in which the cover 14 wraps over and end of and is attached to the main body 12. Each of FIGS. 8 and 9 illustrates the main body 12 independent of the cover 14; FIG. 11 illustrates the cover 14 independent of the main body 12.

Figure 1:
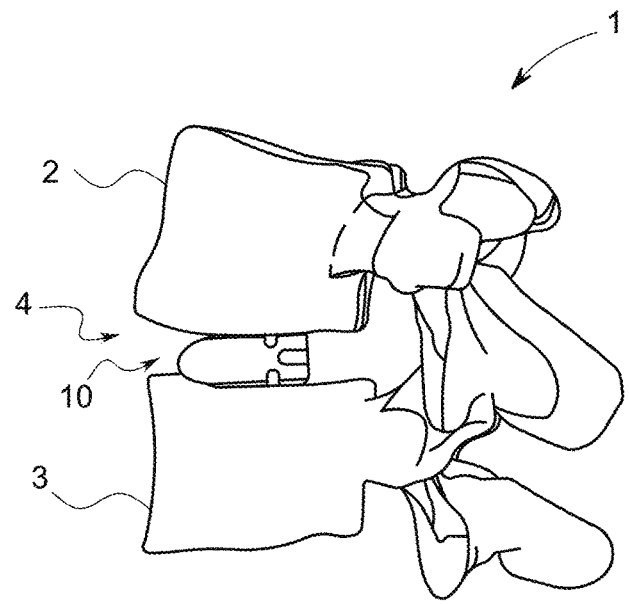
FIG. 1 is a partial side view of a human vertebral column with a first example implantable medical device implanted in the intervertebral space between two adjacent vertebrae.

As illustrated in FIG. 1, the implantable medical device 10 can be implanted in an intervertebral space 4 between adjacent vertebrae 2, 3 of a vertebral column 1 of a human or other vertebrate. Used in this manner, the implantable medical device 10 assists in the maintaining of a desired spacing between and/or fusing of the adjacent vertebrae 2, 3.

The main body 12 has a proximal end 20 and a distal end 22, an upper surface 24 and a lower surface 26, a first lateral surface 28 and a second lateral surface 30. The main body 12 has a circumferential inner wall 32 that defines a passageway 34 that extends from an upper opening 36 cooperatively defined by the upper surface 24 and the proximal surface 40 to a lower opening 38 cooperatively defined by the lower surface 26 and the proximal surface 40. As such, the passageway 34 extends through the entire maximum height h of the main body 12.

As best illustrated in FIG. 8, the proximal end 20 of the main body 12 defines a proximal surface 40 that extends from the upper surface 24 to the lower surface 26 and forms a rounded nose 42. The proximal surface 40 defines a first lateral rib 44 and a second lateral rib 46 that bound a channel 48 that terminates at the upper surface 24 of the main body 12 and the lower surface 26 of the main body 12. In the illustrated embodiment, the first lateral surface 28 and the second lateral surface 30 comprise faceted surfaces. Thus, the first lateral surface 28 includes a proximal portion 28a that is disposed on a plane that tapers inwardly from a plane containing a distal portion 28b. Similarly, the second lateral surface 30 includes a proximal portion 30a that is disposed on a plane that tapers inwardly from a plane containing a distal portion 30b. The inward tapering of the proximal portions 28a, 30a of the first 28 and second 30 lateral surfaces contributes to the formation of the rounded nose 42 on the proximal end 20 of the main body. In the illustrated embodiment, the distal portions 28b, 30b of the first 28 and second 30 lateral surfaces lie on planes that are parallel to, or substantially parallel to, each other.

The distal end 22 of the main body 12 defines a distal surface 50 that extends from the upper surface 24 to the lower surface 26. In the illustrated embodiment, the distal surface 50 lies on a plane that is substantially perpendicular to a plane that contains the upper surface 24 and a plane that contains the lower surface 26. The distal surface 50 defines distal opening 52 that is sized and configured for engagement by an insertion tool or other implement suitable for use during the implantation of the medical device 10. As such, the distal surface 50 can define additional structural features that facilitate engagement between an insertion tool and the distal opening 52, such as a thread that functionally matches a thread on the insertion tool. In the illustrated embodiment, the distal opening 52 is a circular opening suitable for facilitating engagement with an insertion tool having a rod or rod-like shape. It is noted, though, that the distal surface of a main body in an implantable medical device according to a particular embodiment can define other structural features, including openings of different shapes and configurations, that are suitable for facilitating engagement with insertion tools have other structural configurations.

Figure 3:
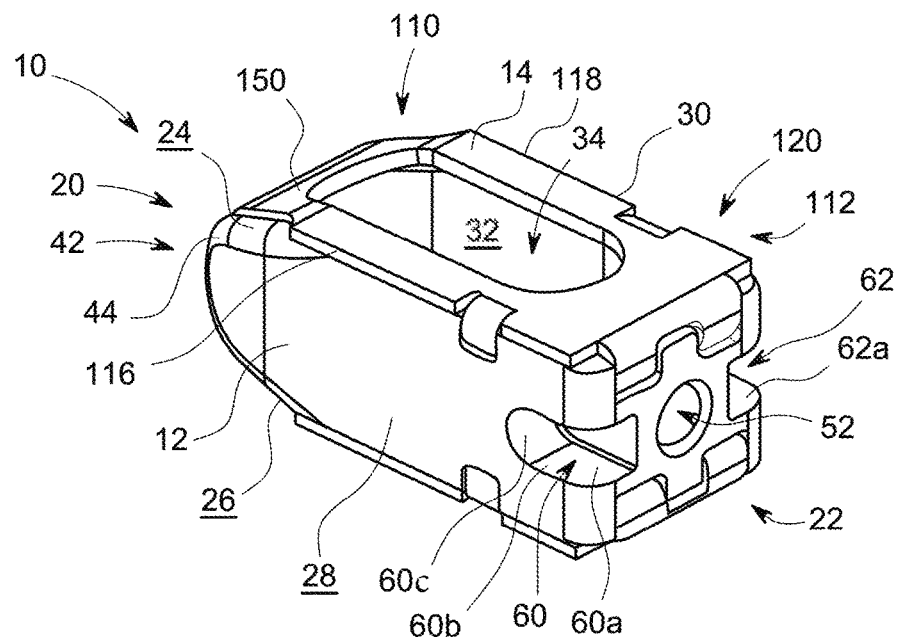
FIG. 3 is another perspective view of the first example implantable medical device.
Figure 4:
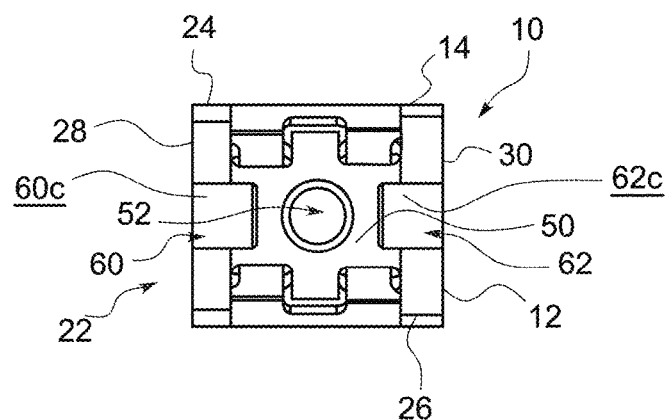
FIG. 4 is an end view of the first example implantable medical device.

As best illustrated in FIGS. 3 and 9, the distal surface 50 and the first lateral surface 28 cooperatively define first pocket 60. Similarly, the distal surface 50 and the second lateral surface 30 cooperatively define second pocket 62. Each of the pockets 60, 62 comprise a cavity in communication with the distal surface 50 and one of the first 28 and second 30 lateral surfaces of the main body 12. The first pocket 60 has a distal portion 60a that is opens to the distal surface 50 and a proximal portion 60b that terminates in a rounded proximal surface 60c. Similarly, the second pocket 62 has a distal portion 62a that opens to the distal surface 50 and a proximal portion 62b that terminates in a rounded proximal surface 62c. Each of the pockets 60, 62 is sized and configured for engagement by an insertion tool or other implement suitable for use during the implantation of the medical device 10. Any suitable number of pockets can be included in a medical device according to a particular embodiment. Inclusion of two pockets, such as pockets 60, 62, opposably positioned on the distal surface 50 is considered advantageous, though, as it facilitates engagement of the implantable medical device 10 using an implement adapted for grabbing with pincer-like action. Inclusion of the pockets 60, 62 and the distal opening 52 is considered particularly advantageous as the combination of these structural features facilitates engagement of the implantable medical device 10 with a variety of implements.

Figure 5:
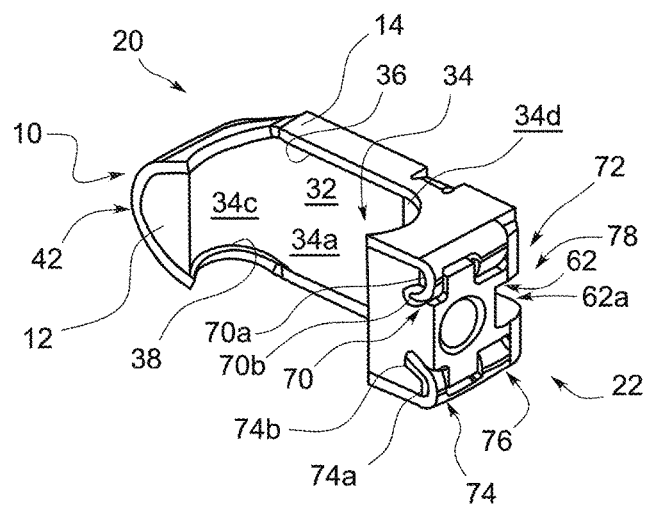
FIG. 5 is a perspective cross-sectional view of the first example implantable medical device.
Figure 6:
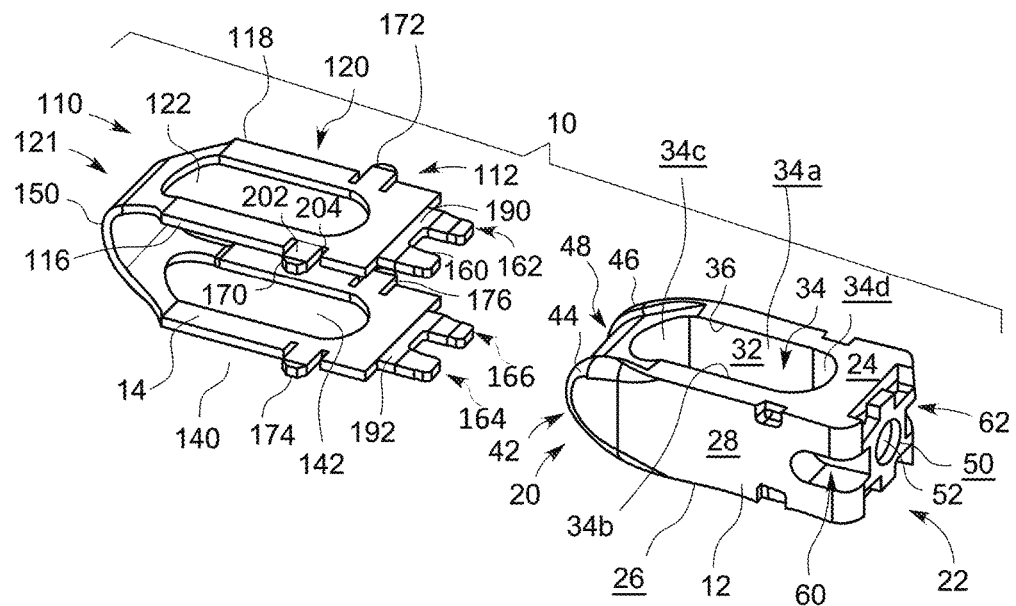
FIG. 6 is an exploded view of the first example implantable medical device.

As best illustrated in FIGS. 5 and 9, the distal surface 50 and the upper surface 24 of the main body 12 cooperatively define cavities 70 and 72. Similarly, the distal surface 50 and the lower surface 26 cooperatively define cavities 74, 76. As best illustrated in FIG. 5, each of the cavities 70, 72, 74, 76 defines a first portion that is continuous with the distal surface 50 and either the upper surface 24 or the lower surface 26 and a second portion that extends from the first portion into the main body 12 and away from the distal surface 50 and either the upper surface 24 or the lower surface 26. Thus, cavity 70 has a first portion 70a that is continuous with the distal surface 50 and the upper surface 24 of the main body 12 and a second portion 70b that extends from the first portion 70a into the main body 12 and away from the distal surface 50 and the upper surface 24. Similarly, cavity 72 has a first portion that is continuous with the distal surface 50 and the upper surface 24 of the main body 12 and a second portion that extends from the first portion into the main body 12 and away from the distal surface 50 and the upper surface 24. Similarly, cavity 74 has a first portion that is continuous with the distal surface 50 and the lower surface 26 of the main body 12 and a second portion that extends from the first portion into the main body 12 and away from the distal surface 50 and the lower surface 26. Similarly, cavity 76 has a first portion that is continuous with the distal surface 50 and the lower surface 26 of the main body 12 and a second portion that extends from the first portion into the main body 12 and away from the distal surface 50 and the lower surface 26. As will be described in more detail below, cavities 70, 72, 74, 76 comprise a first plurality of cavities 78, or distal plurality of cavities, that is adapted for receiving a plurality of distal tabs 168 of the cover 14 of the implantable medical device 10.

As best illustrated in FIGS. 8 and 9, the first lateral surface 28 cooperatively defines cavity 80 with the upper surface 24 of the main body 12 and cavity 82 with the lower surface 26 of the main body 12. Similarly, the second lateral surface 30 cooperatively defines cavity 84 with the upper surface 24 of the main body 12 and cavity 86 with the lower surface 26 of the main body 12. Each of the cavities 80, 82, 84, 86 has a similar structure to the cavities 70, 72, 74, 76 of the first plurality of cavities 78. Thus, each of the cavities 80, 82 defines a first portion that is continuous with the first lateral surface 28 and either the upper surface 24 or the lower surface 26 and a second portion that extends from the first portion into the main body 12 and away from the first lateral surface 28 and either the upper surface 24 or the lower surface 26. Similarly, each of the cavities 84, 86 defines a first portion that is continuous with the second lateral surface 30 and either the upper surface 24 or the lower surface 26 and a second portion that extends from the first portion into the main body 12 and away from the second lateral surface 30 and either the upper surface 24 or the lower surface 26. Thus, cavity 80 has a first portion 80a that is continuous with the first lateral surface 28 and the upper surface 24 of the main body 12 and a second portion 80b that extends from the first portion 80a into the main body 12 and away from the first lateral surface 28 and the upper surface 24. Cavity 82 has a first portion 82a that is continuous with the first lateral surface 28 and the lower surface 26 of the main body 12 and a second portion 82b that extends from the first portion 82a into the main body 12 and away from the first lateral surface 28 and the lower surface 26. Cavity 84 has a first portion 84a that is continuous with the second lateral surface 30 and the upper surface 24 of the main body 12 and a second portion 84b that extends from the first portion 84a into the main body 12 and away from the second lateral surface 30 and the upper surface 24. Cavity 86 has a first portion 86a that is continuous with the second lateral surface 30 and the lower surface 26 of the main body 12 and a second portion 86b that extends from the first portion 86a into the main body 12 and away from the second lateral surface 30 and the lower surface 26. As will be described in more detail below, cavities 80, 82, 84, 86 comprise a second plurality of cavities 88, or lateral plurality of cavities, that is adapted for receiving a plurality of lateral tabs 178 of the cover 14 of the implantable medical device 10.

While the illustrated embodiment includes four cavities 70, 72, 74, and 76 in the first plurality of cavities 78 and four cavities 80, 82, 84, 86 in the second plurality of cavities 88, any suitable number of cavities can be included in an implantable medical device according to a particular embodiment. A skilled artisan will be able to select a suitable number of cavities for inclusion in a particular implantable medical device based on various considerations, including the number of tabs provided by the cover included in the implantable medical device. Examples of suitable numbers of cavities for the first, or distal, plurality of cavities include, but are not limited to, 1, 2, 3, 4, 5 and 6 cavities. Examples of suitable numbers of cavities for the second, or lateral, plurality of cavities include, but are not limited to, 1, 2, 3, 4, 5 and 6 cavities. For each plurality of cavities, it is considered advantageous to include an even number of cavities to ensure structural balance, though this is not considered necessary. Also, it is noted that, while the illustrated embodiment includes both first 78 and second 88 pluralities of cavities, each plurality of cavities is considered optional. For example, a main body in an implantable medical device according to a particular embodiment may define only the distal plurality of cavities or only the lateral plurality of cavities.

The main body 12 has an inner wall 32 that defines passageway 34. The passageway 34 extends from an upper opening 36 cooperatively defined by the upper surface 24 and the proximal surface 40 to a lower opening 38 cooperatively defined by the lower surface 26 and the proximal surface 40. The passageway in an implantable medical device according to a particular embodiment can have any suitable structural configuration and a skilled artisan will be able to select a suitable configuration for a passageway in a particular implantable medical device based on various considerations, including any desired extent of bone ingrowth following implantation of the implantable medical device. In the illustrated embodiment, the passageway 34 is generally stadium-shaped, with parallel lateral sides 34a, 34b and rounded ends 34c, 34d. This structural configuration is considered advantageous at least because it balances a desire to provide a large area for bone ingrowth with a need to maintain structural integrity of the main body 12. Examples of other suitable structural configurations for a passageway in an implantable medical device according to a particular embodiment include a passageway that has a square or substantially square cross-sectional configuration, a passageway that has a rectangular or substantially rectangular cross-sectional configuration, a passageway that has an elliptical or substantially elliptical cross-sectional configuration, and any other suitable structural configuration. Of note, the passageway 34 in the illustrated embodiment extends into the proximal end 20 of the main body 12 such that a portion of the proximal surface 40 cooperates with the upper surface 24 to define the upper opening 36 and a portion of the proximal surface 40 cooperates with the lower surface 26 to define the lower opening 38.

In the illustrated embodiment, the upper surface 24 lies on a plane that is perpendicular to, or substantially perpendicular to, planes that individually contain the first 28 and second 30 lateral surfaces. Similarly, the lower surface 26 lies on a plane that is perpendicular to, or substantially perpendicular to, planes that individually contain the first 28 and second 30 lateral surfaces. It is noted, though, that one or both of the upper and lower surfaces of a main body of an implantable medical device according to a particular embodiment can define a curvilinear surface. Furthermore, one or both of the first and second lateral surfaces of a main body of an implantable medical device according to a particular embodiment can define a curvilinear surface, either as a whole or in one of the proximal and distal portions of the particular lateral surface. Other configurations are also contemplated. For example, a main body in an implantable medical device according to an embodiment can have an upper surface and/or a lower surface that lie(s) on a plane that is disposed at a non-perpendicular angle to an axis of the medical device, such as a lengthwise or widthwise axis of the implantable medical device. Similarly, a main body in an implantable medical device according to an embodiment can have a first and/or a second lateral surface that lie(s) on a plane that is disposed at a non-perpendicular angle to an axis of the medical device, such as a lengthwise or widthwise axis of the implantable medical device. Implantable medical devices according to these embodiments can be characterized as having one or more tapered surfaces and are suitable for use as lordotic implantable medical devices.

Figure 10:
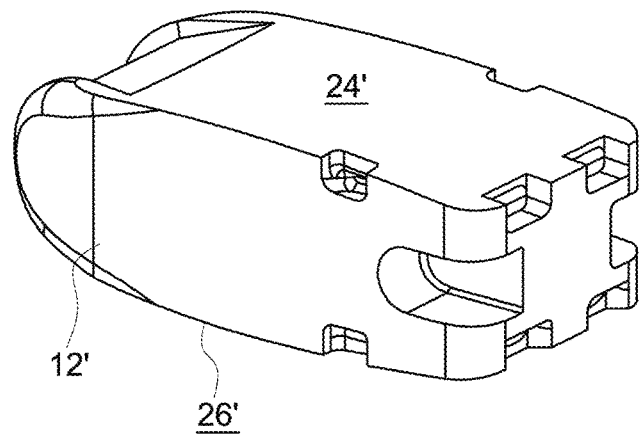
FIG. 10 is a perspective view of an alternative main body component for use in an implantable medical device.

For example, FIG. 10 illustrates an alternate main body 12' having a curvilinear upper surface 24' and a curvilinear lower surface 26'. This configuration may be advantageous for use when one or both vertebrae adjacent an intervertebral space into which an implantable medical device is to be placed have rounded or irregular surfaces that may make it difficult to position an implantable medical device with a main body having substantially flat upper and lower surfaces within the intervertebral space.

Figure 2:
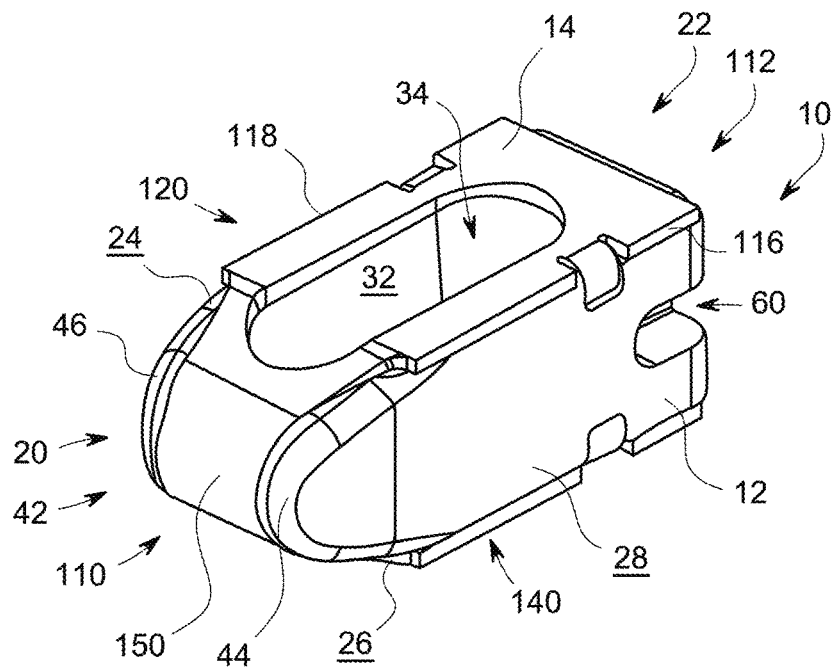
FIG. 2 is a perspective view of the first example implantable medical device.

As best illustrated in FIG. 11, the cover 14 has a proximal end 110, a distal end 112, a first lateral side 116, a second lateral side 118, an upper portion 120 and a lower portion 140 integrally formed with a strut 150 that extends between the upper portion 120 and lower portion 140. Generally, the cover 14 is a section of a sheet of material formed to have desired structural features and bent at the strut 150 to form a rounded nose 121 at the proximal end 110 and to position the upper portion 120 opposite the lower portion 140. This configuration gives the cover 14 a closed proximal end 110 in which the upper portion 120 and lower portion 140 are connected to each other and an open distal end 112 in which the upper portion 120 and lower portion 140 are not connected to each other and are physically spaced from each other. When the cover is not attached to the main body 12 in an assembled implantable medical device, the open distal end 112 of the cover 14 has the upper portion 120 and lower portion 140 separated from each other by a space. This is considered advantageous at least because the open distal end 112 allows the implantable medical device 10, when under load, to approximate the Young's Modulus of the main body even when the cover 14 is formed of a material having a higher Young's Modulus than that of the main body 12, as described in more detail below. The inclusion of an open end is considered important to the desired functionality of the implantable medical device in embodiments in which the main body has a different Young's Modulus than the Young's Modulus of the cover. When attached to a main body 12, the cover 14 generally conforms to the main body 12 within a fully assembled implantable medical device 10. As best illustrated in FIGS. 2 and 3, the cover 14 is attached to the main body 12 in the assembled implantable medical device 10, as described in more detail below.

The cover 14 defines an upper opening 122 in the upper portion 120 and a lower opening 142 in the lower portion 140. Each of the upper opening and the lower opening in an implantable medical device according to a particular embodiment can have any suitable size and configuration, and a skilled artisan will be able to select a suitable size and configuration for each of the upper opening and lower opening based on various considerations, including considerations relating to the visualization of the implantable medical device and considerations relating to the ability to access the passageway defined by the main body of the implantable medical device. In the illustrated embodiment, each of the upper opening 122 and lower opening 142 have a size and configuration that is substantially the same as that of the corresponding Also, the upper opening 122 and lower opening 142 in the illustrated embodiment have substantially the same size and configuration. Thus, when bent at the strut, as illustrated in FIG. 11, the upper opening 122 axially aligned with the lower opening 142.

The cover 14 defines tabs 160, 162, 164, 166 that extend distally away from the distal end 112. The cover 14 also defines tabs 170, 172 that extend laterally away from the first lateral side 116, and tabs 174, 176 that extend laterally away from the second lateral side 118. Tabs 160, 162, 164, 166 comprise a first plurality of tabs 168, or distal plurality of tabs. Tabs 170, 172, 174, 176 comprise a second plurality of tabs 178, or lateral plurality of tabs. The second plurality of tabs 178 comprises a first set of tabs 180 that includes tabs 170 and 172 that extend laterally away from the first lateral side 116 of the cover 14 and a second set of tabs 172 that extend laterally away from the second lateral side 118 of the cover 14.

Figure 7:
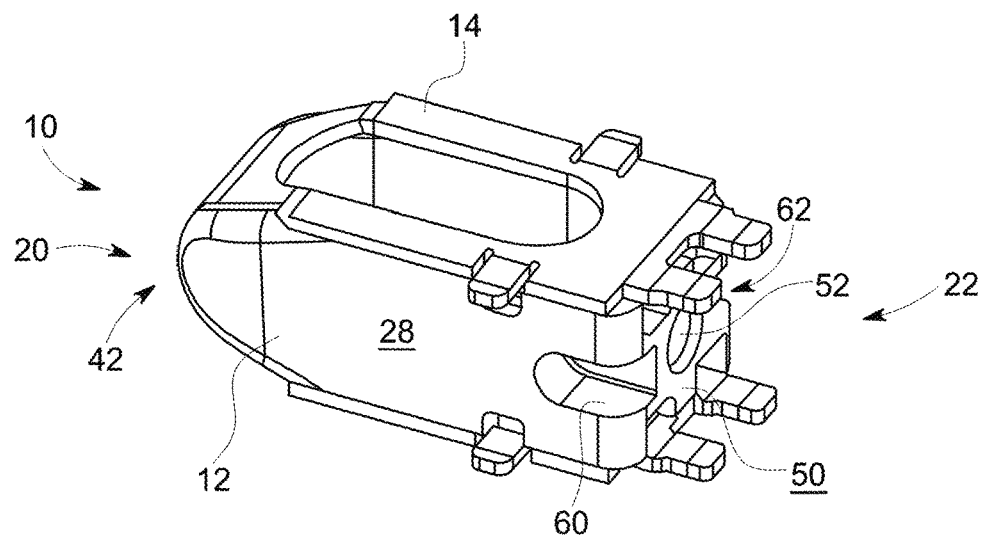
FIG. 7 is a perspective view of the first example implantable medical device at an interim point during manufacturing.

As best illustrated in FIG. 7, each of the tabs 160, 162, 164, 166, 170, 172, 174, 176 aligns with, and is sized and configured to be inserted into, a corresponding cavity 70, 72, 74, 76, 80, 82, 84, 86 defined by the main body 12 during fabrication of the implantable medical device 10. As such, the tabs in a cover according to a particular embodiment can have any suitable size and structural configuration, but should be sized and configured to allow the insertion of each tab into a corresponding cavity in the main body of the particular implantable medical device. A skilled artisan will be able to determine an appropriate size and configuration for all tabs in an implantable medical device according to a particular embodiment based on various considerations, particularly the size and configuration of the cavities defined by the main body in the particular implantable medical device. In the illustrated embodiment, distal tabs 160, 162 extend distally from a common base 190 on the distal edge of the upper portion 120 of cover 14. Similarly, distal tabs 164, 166 extend distally from a common base 192 on the distal edge of the lower portion 140 of cover 14. Lateral tab 170 extends from a base 202 of a notch 204 in a first lateral edge of the upper portion 120 of the cover 14. Lateral tab 172 extends from a base 206 of a notch 208 in a second lateral edge of the lower portion 140 of the cover 14. Lateral tab 174 extends from a base 210 of a notch 212 in a first lateral edge of the upper portion 120 of the cover 14. Lateral tab 176 extends from a base 214 of a notch 216 in a second lateral edge of the lower portion 140 of the cover 14.

While the illustrated embodiment includes four distal tabs 160, 162, 164, 166 in the first plurality of tabs 168 and four tabs 170, 172, 174, 176 in the second plurality of tabs 178, any suitable number of tabs can be included in a cover for an implantable medical device according to a particular embodiment. A skilled artisan will be able to select a suitable number of tabs for inclusion in a particular implantable medical device based on various considerations, including the number of cavities provided by the main body included in the implantable medical device. Examples of suitable numbers of tabs for the first plurality of tabs include, but are not limited to, 1, 2, 3, 4, 5 and 6 tabs. Examples of suitable numbers of tabs for the second plurality of tabs include, but are not limited to, 1, 2, 3, 4, 5 and 6 tabs. For each plurality of tabs, it is considered advantageous to include an even number of tabs to ensure structural balance, though this is not considered necessary. Also, it is noted that, while the illustrated embodiment includes both first 168 and second 178 pluralities of tabs, each plurality of tabs is considered optional. For example, a cover in an implantable medical device according to a particular embodiment may define only a distal plurality of tabs or only a lateral plurality of tabs.

As best illustrated in FIGS. 2, 3, 4 and 5, in the assembled implantable medical device 10, the strut 150 of the cover 14 is disposed within the channel 48 and between the first lateral rib 44 and the second lateral rib 46 of the main body 12. Also, each of the distal tabs 160, 162, 164, 166 is bent inwardly such that a portion of each individual tab 160, 162, 164, 166 is disposed in the first portion of a respective distal cavity 70, 72, 74, 76 and such that a portion of each individual tab 160, 162, 164, 166 is disposed in the second portion of the respective distal cavity 70, 72, 74, 76. Similarly, each of the lateral tabs 170, 172, 174, 176 is bent inwardly such that a portion of each individual tab 170, 172, 174, 176 is disposed in the first portion of a respective lateral cavity 80, 82, 84, 86 and such that a portion of each individual tab 170, 172, 174, 176 is disposed in the second portion of the respective distal cavity 80, 82, 84, 86.

In all examples, each of the main body and cover can be formed of any suitable material, including presently known and later-developed materials for use in implantable medical devices suitable for implantation in spaces between bones, including within intervertebral spaces. A skilled artisan will be able to select an appropriate material or materials for each component of an implantable medical device according to a particular embodiment based on various considerations, including, but not limited to, considerations relating to the ability to visualize the device using any desirable visualization techniques and/or equipment, considerations relating to any bone graft of other material that may be used in conjunction with the implantable medical device during treatment, and the anatomical location at which the implantable medical device is to be implanted. Examples of suitable materials include, but are not limited to, polyetheretherketone ("PEEK"), stainless steel, nickel-cobalt-chromium alloys, polymeric materials, and any of a number of biocompatible materials.

The main body and cover can be formed of the same or different materials. It is considered advantageous, though, to form these components of different materials to facilitate handling and image properties of implantable medical devices. For example, the inventors have determined that an implantable medical device that includes a main body formed of a radiolucent material, such as PEEK, and a cover that is formed of a radiopaque materials, such as stainless steel, titanium, or other suitable radiopaque material, provides desirable handling and visualization properties for the implantable medical device. Commercially pure, grade 2 ("CP-2") titanium is considered a particularly advantageous material for the cover. It is also noted that the visualization properties of implantable medical devices according to embodiments are particularly enhanced with the inclusion of a cover having a closed proximal end, such as the rounded nose in the illustrated embodiment, and an open distal end. This configuration provides for desirable three-dimensional orienting of the implantable medical device when observed under visualization, facilitating its placement in a treatment procedure. It is also considered advantageous to form the main body from a material having a different Young's Modulus than the Young's Modulus of the material from which the cover is formed. It is considered particularly advantageous to form the main body from a material having a lower Young's Modulus than the Young's Modulus for the material from which the cover is formed. Furthermore, the inventors have determined that the inclusion of a cover having an open end, such as described above, and a higher Young's Modulus than the Young's Modulus of the material from which the main body is formed is advantageous at least because this structural arrangement of elements with these relative physical properties allows the implantable medical device, when under load, to approximate the lower Young's Modulus of the main body.

The main body and cover can be formed using conventional forming and/or manufacturing techniques and a skilled artisan will be able to select suitable techniques based, at least, upon the particular material selected for each element. The cover, it is noted, can be formed from sheet stock using conventional tools and equipment for working with sheet stock, such as a press brake. Also, the openings in the cover used in an embodiment can be formed in sheet stock using conventional processes and techniques, such as chemical etching and laser cutting. It is also noted that it is considered advantageous to subject the cover to one or more surface finish and/or treatment processes, preferably before attachment to the main body during fabrication. The inventors have determined that the cover is less likely to delaminate from the main body when the cover has been subjected to a surface treatment process. Furthermore, surface finishing and/or treatment can provide other benefits expected from such processes, such as resistance to back-out and migration and facilitation of bone ingrowth once the implantable medical device is positioned at a point of treatment. If desired, therefore, the cover can be subjected to any desired surface treatment and/or surface finishing process, such as machining, laser micro-machining, knurling, chemical etching, and photochemical etching prior to attachment to the main body during fabrication. It is considered advantageous to perform any desired surface treatments and/or finishing processes on flat stock prior to cutting openings and forming the flat stock into the final structural configuration for the cover.

Figure 12:
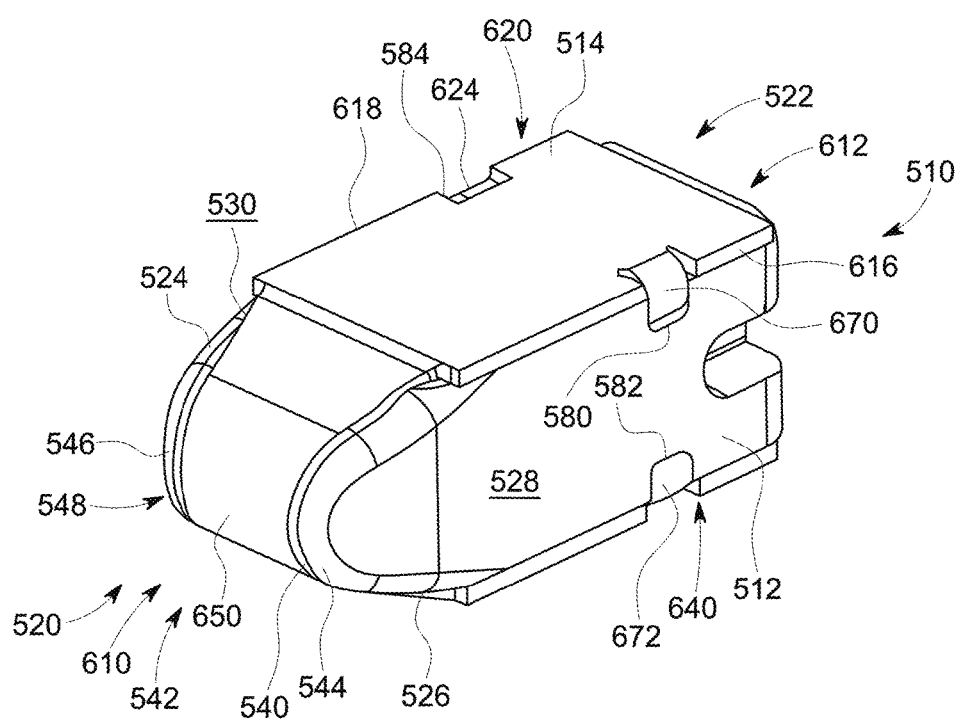
FIG. 12 is a perspective view of a second example implantable medical device.

FIG. 12 illustrates another example implantable medical device 510. The implantable medical device 510 is identical to the first implantable medical device 10 described above, except as detailed below. Thus, the implantable medical device 510 includes a main body 512 and a cover 514. The implantable medical device 510 is a laminate structure in which the cover 514 wraps over an end of and is attached to the main body 512. The main body 512 has a proximal end 520 and a distal end 522, an upper surface 524 and a lower surface 526, a first lateral surface 528 and a second lateral surface 530. The proximal end 520 of the main body 512 defines a proximal surface 540 that extends from the upper surface 524 to the lower surface 526 and forms a rounded nose 542. The proximal surface 540 defines a first lateral rib 544 and a second lateral rib 546 that bound a channel 548 that terminates at the upper surface 524 of the main body 512 and the lower surface 526 of the main body 512. The cover 514 has a proximal end 610, a distal end 612, a first lateral side 616, a second lateral side 618, an upper portion 620 and a lower portion 640 integrally formed with a strut 650 that extends between the upper portion 620 and lower portion 640. Generally, the cover 514 conforms to the main body 512 within the fully assembled implantable medical device 510. The cover 514 is attached to the main body 512 in the assembled implantable medical device 510 via tabs 670, 672, 674 defined by the cover 514 that are seated within cavities 580, 582, 584 defined by the main body 512.

In this embodiment, the main body 512 is a solid member that does not define a passageway that extends through a thickness or height of the main body 512. Furthermore, each of the upper portion 620 and lower portion 640 of the cover 514 defines a solid section of material that does not define an opening that extends through a width or height of the cover 514. With these modifications of the main body 510 and cover 514, the implantable medical device 510 is particularly well-suited for applications where it is not necessary or desirable to place any material, such as bone graft material, within an inner portion of the implantable medical device.

Figure 13:
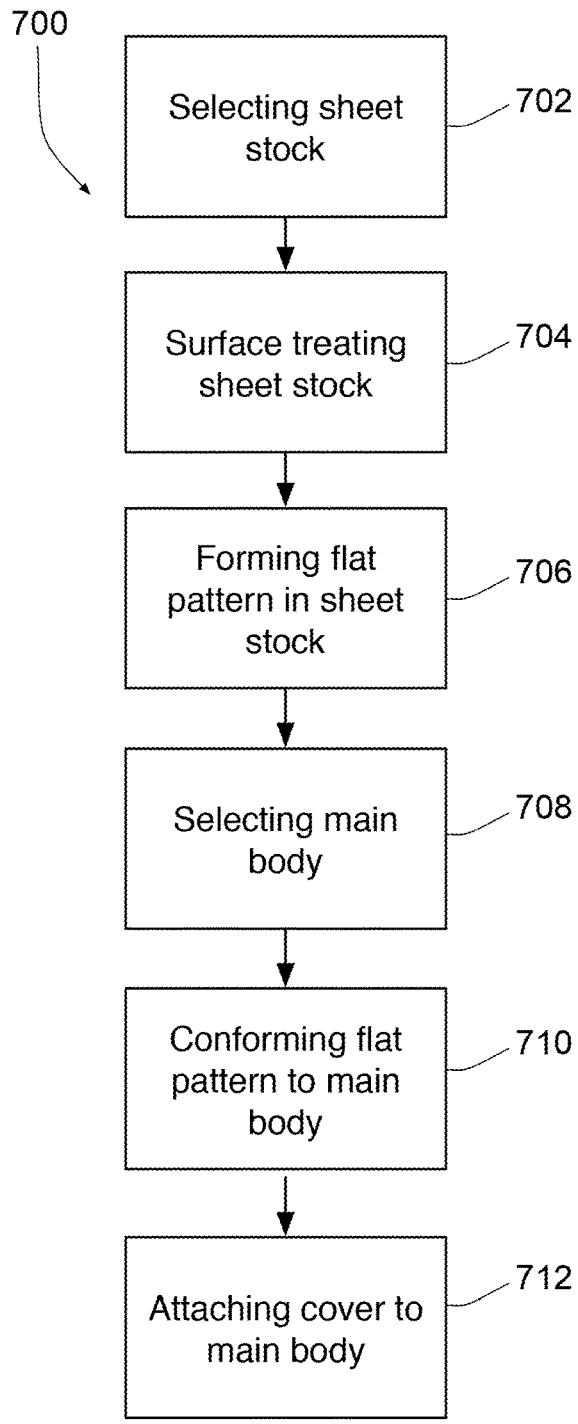
FIG. 13 is a flowchart representation of an example method of manufacturing implantable medical devices.

Methods of manufacturing implantable medical devices are also provided. FIG. 13 illustrates a flowchart representation of an example method of manufacturing 700 an implantable medical device.

One step 702 comprises selecting sheet stock suitable for use as a cover in an implantable medical device. Any suitable sheet stock can be selected, and a skilled artisan will be able to determine appropriate parameters and selection guidelines for this step based on various considerations, including any intended position within the body at which the implantable medical device is intended to be used, any desired relative materials properties between the cover and the main body in the implantable medical device being fabricated by performance of the method, and other considerations. As noted above, this step can be performed by selecting a section of sheet stock of CP-2 titanium or other suitable material.

Another step 704 comprises surface treating the selected sheet stock. This step is considered optional, and need only be performed if it is desired to have a cover in the implantable medical device being fabricated by performance of the method that has had a surface treatment or finish applied to it. If included, this step can be performed using any suitable technique(s), process(es), equipment, tools, and/or materials and a skilled artisan will be able to select appropriate technique(s), process(es), equipment, tools, and/or materials for performance of the step based on various considerations, including the desired surface treatment and/or finish for a cover in a particular implantable medical device. Examples of suitable processes that can be performed for the performance of this step include, but are not limited to, machining, laser micro-machining, knurling, chemical etching, and photochemical etching.

Another step 706 comprises forming a flat pattern in the sheet stock. This step is considered optional, and need only be performed if it is desired to have a cover in the implantable medical device being fabricated by performance of the method that has a pattern formed in it that is different than the general configuration of the selected sheet stock. For example, if it is desirable to have openings, tabs, and/or other structural features in the cover of the implantable medical device being fabricated, this step can be included. If included, this step can be performed using any suitable technique(s), process(es), equipment, tools, and/or materials and a skilled artisan will be able to select appropriate technique(s), process(es), equipment, tools, and/or materials for performance of the step based on various considerations, including the material of the selected sheet stock and the desired structural configuration for a cover in a particular implantable medical device. Examples of suitable processes that can be performed for the performance of this step include, but are not limited to, machining, chemical etching, and laser cutting.

Another step 708 comprises selecting a main body. Any suitable main body can be selected, and a skilled artisan will be able to determine appropriate parameters and selection guidelines for this step based on various considerations, including any intended position within the body at which the implantable medical device is intended to be used, any desired relative materials properties between the cover and the main body in the implantable medical device being fabricated by performance of the method, and other considerations. As noted above, this step can be performed by selecting a main body formed from PEEK or other suitable material.

Another step 710 comprises conforming the flat pattern to the main body. This step is considered critical, and must be performed. This step can be performed using any suitable technique(s), process(es), equipment, tools, and/or materials and a skilled artisan will be able to select appropriate technique(s), process(es), equipment, tools, and/or materials for performance of the step based on various considerations, including the materials of the selected sheet stock and the main body. Mechanically deforming the flat pattern to conform to the main body as a cover using a press brake or other similar equipment is considered suitable for performing this step.

Another step 712 comprises attaching the flat pattern to the main body as a cover to produce an implantable medical device. This step is also considered critical, and must be performed. It is noted, though, that this step can be accomplished by performance of the step 710 of conforming the flat pattern to the main body. For example, while conforming the flat pattern to the main body, structural features of the flat pattern, such as tabs, can be manipulated to engage structural features of the main body, such as cavities, to effectively attach the flat pattern to the main body as a cover. In this example, both steps 710 and 712 are performed in one operation. Alternatively, this step can be performed as a separate step from the step 710 of conforming the flat pattern to the main body. In these example methods, this step can be performed using any suitable technique(s), process(es), equipment, tools, and/or materials and a skilled artisan will be able to select appropriate technique(s), process(es), equipment, tools, and/or materials for performance of the step based on various considerations, including the materials of the selected sheet stock and the main body. Securing the flat pattern to the main body using suitable connectors, adhesives or other means for connecting a flat pattern to a main body is considered a suitable technique for performance of this step in these methods.

It is noted that the steps in a particular method of manufacturing an implantable medical device in accordance with the invention can be performed in any suitable order, and a skilled artisan contemplating performance of a method will be able to select an appropriate order based on various considerations, such as any desired levels of manufacturing efficiency and/or waste, among others. It is considered advantageous to perform the steps in the order presented in FIG. 13 and described herein, but any order beyond that which is required by the steps themselves is considered optional. For example, the step of selecting sheet stock must be performed before the steps of surface treating the sheet stock and forming the flat pattern in the sheet stock. Also, the step of selecting the main body must be performed before the step of conforming the flat pattern to the main body.

Once the flat pattern has been attached to the main body as a cover, the implantable medical device has been fabricated. It is noted, though, that additional processing of the implantable medical device may be desired and/or required prior to use, such as sterilization and other processing.

The foregoing detailed description refers to example apparatuses and methods and includes any presently contemplated best mode for practicing the inventive apparatuses and methods. The description and the appended drawings illustrating the described apparatuses and methods are intended only to provide examples and not to limit the scope of the claims in any manner.

What is claimed is:

1. An implantable medical device, comprising:
a main body defining an upper surface, a lower surface, a proximal surface, a distal surface, a first lateral surface, and a second lateral surface, the proximal surface defining first and second lateral ribs and a channel bounded by the first and second lateral ribs;
a cover attached to the main body, the cover comprising an upper portion, a lower portion, and a strut extending between and connecting the upper and lower portions, the strut disposed within the channel of the main body;
wherein the upper surface of the main body defines an upper main body opening and the lower surface of the main body defines a lower main body opening;
wherein the main body has an inner circumferential wall defining a passageway extending through the main body from the upper main body opening to the lower main body opening;
wherein the upper portion of the cover defines an upper cover opening and the lower portion of the cover defines a lower cover opening;
wherein the upper cover opening has substantially the same size and configuration of the upper main body opening;
wherein the lower cover opening has substantially the same size and configuration of the lower main body opening;
wherein the main body defines a cavity;
wherein the cover defines a tab that extends into the cavity; and
wherein the cavity has a first portion and a second portion, the first portion being continuous with the distal surface and one of the upper surface and the lower surface, and the second portion extending away from the first portion into the main body and away from the distal surface and the one of the upper surface and the lower surface.

2. An implantable medical device, comprising:
a main body defining an upper surface, a lower surface, a proximal surface, a distal surface, a first lateral surface, and a second lateral surface, the proximal surface defining first and second lateral ribs and a channel bounded by the first and second lateral ribs;
a cover attached to the main body, the cover comprising an upper portion, a lower portion, and a strut extending between and connecting the upper and lower portions, the strut disposed within the channel of the main body;
wherein the upper surface of the main body defines an upper main body opening and the lower surface of the main body defines a lower main body opening;
wherein the main body has an inner circumferential wall defining a passageway extending through the main body from the upper main body opening to the lower main body opening;
wherein the upper portion of the cover defines an upper cover opening and the lower portion of the cover defines a lower cover opening;
wherein the upper cover opening has substantially the same size and configuration of the upper main body opening;
wherein the lower cover opening has substantially the same size and configuration of the lower main body opening;
wherein the main body defines a cavity;
wherein the cover defines a tab that extends into the cavity; and
wherein the cavity has a first portion and a second portion, the first portion being continuous with the first lateral surface and one of the upper surface and the lower surface, and the second portion extending away from the first portion into the main body and away from the first lateral surface and the one of the upper surface and the lower surface.

3. An implantable medical device, comprising:
a main body defining an upper surface, a lower surface, a proximal surface, a distal surface, a first lateral surface, and a second lateral surface, the proximal surface defining first and second lateral ribs and a channel bounded by the first and second lateral ribs;
a cover attached to the main body, the cover comprising an upper portion, a lower portion, and a strut extending between and connecting the upper and lower portions, the strut disposed within the channel of the main body;
wherein the upper surface of the main body defines an upper main body opening and the lower surface of the main body defines a lower main body opening;
wherein the main body has an inner circumferential wall defining a passageway extending through the main body from the upper main body opening to the lower main body opening;
wherein the upper portion of the cover defines an upper cover opening and the lower portion of the cover defines a lower cover opening;
wherein the upper cover opening has substantially the same size and configuration of the upper main body opening;
wherein the lower cover opening has substantially the same size and configuration of the lower main body opening;
wherein the main body defines a first plurality of cavities;
wherein the cover defines a plurality of tabs, each tab of the plurality of tabs extending into one of the first plurality of cavities; and
wherein each cavity of the first plurality of cavities has a first portion and a second portion, the first portion being continuous with the distal surface and one of the upper surface and the lower surface, and the second portion extending away from the first portion into the main body and away from the distal surface and the one of the upper surface and the lower surface.

4. An implantable medical device, comprising:
a main body defining an upper surface, a lower surface, a proximal surface, a distal surface, a first lateral surface, and a second lateral surface, the proximal surface defining first and second lateral ribs and a channel bounded by the first and second lateral ribs;

a cover attached to the main body, the cover comprising an upper portion, a lower portion, and a strut extending between and connecting the upper and lower portions, the strut disposed within the channel of the main body;

wherein the upper surface of the main body defines an upper main body opening and the lower surface of the main body defines a lower main body opening;

wherein the main body has an inner circumferential wall defining a passageway extending through the main body from the upper main body opening to the lower main body opening;

wherein the upper portion of the cover defines an upper cover opening and the lower portion of the cover defines a lower cover opening;

wherein the upper cover opening has substantially the same size and configuration of the upper main body opening;

wherein the lower cover opening has substantially the same size and configuration of the lower main body opening;

wherein the main body defines a first plurality of cavities;

wherein the cover defines a plurality of tabs, each tab of the plurality of tabs extending into one of the first plurality of cavities; and wherein each cavity of the first plurality of cavities has a first portion and a second portion, the first portion being continuous with the first lateral surface and one of the upper surface and the lower surface, and the second portion extending away from the first portion into the main body and away from the first lateral surface and the one of the upper surface and the lower surface.

5. An implantable medical device, comprising:

a main body defining an upper surface, a lower surface, a proximal surface, a distal surface, a first lateral surface, and a second lateral surface, the proximal surface defining first and second lateral ribs and a channel bounded by the first and second lateral ribs;

a cover attached to the main body, the cover comprising an upper portion, a lower portion, and a strut extending between and connecting the upper and lower portions, the strut disposed within the channel of the main body;

wherein the upper surface of the main body defines an upper main body opening and the lower surface of the main body defines a lower main body opening;

wherein the main body has an inner circumferential wall defining a passageway extending through the main body from the upper main body opening to the lower main body opening;

wherein the upper portion of the cover defines an upper cover opening and the lower portion of the cover defines a lower cover opening;

wherein the upper cover opening has substantially the same size and configuration of the upper main body opening;

wherein the lower cover opening has substantially the same size and configuration of the lower main body opening;

wherein the main body defines a first plurality of cavities and a second plurality of cavities;

wherein each cavity of the first plurality of cavities has a first portion and a second portion, the first portion being continuous with the distal surface and one of the upper surface and the lower surface, and the second portion extending away from the first portion into the main body and away from the distal surface and the one of the upper surface and the lower surface;

wherein each cavity of the second plurality of cavities has a first portion and a second portion, the first portion being continuous with the first lateral surface and one of the upper surface and the lower surface, and the second portion extending away from the first portion into the main body and away from the first lateral surface and the one of the upper surface and the lower surface;

wherein the cover defines a first plurality of tabs and a second plurality of tabs, each tab of the first plurality of tabs extending into one of the first plurality of cavities and each tab of the second plurality of tabs extending into one of the second plurality of cavities.

6. An implantable medical device, comprising:

a radiolucent main body defining an upper surface, a lower surface, a proximal surface, a distal surface, a first lateral surface, and a second lateral surface,
the upper surface defining an upper main body opening, the lower surface defining a lower main body opening, and the proximal surface forming a rounded nose and defining first and second lateral ribs and a channel bounded by the first and second lateral ribs;
the distal surface of the main body at least partially defining a first plurality of cavities;
the first lateral surface of the main body at least partially defining a second plurality of cavities; and
the main body having an inner circumferential wall defining a passageway extending through the main body from the upper main body opening to the lower main body opening; and a radiopaque cover attached to the main body, the cover comprising an upper portion defining an upper cover opening, a lower portion defining a lower cover opening, and a strut extending between and connecting the upper and lower portions, the strut disposed within the channel of the main body,
the cover defining a first plurality of tabs, each tab of the first plurality of tabs disposed within a cavity of the first plurality of cavities; and
the cover defining a second plurality of tabs, each tab of the second plurality of tabs disposed within a cavity of the second plurality of cavities;

wherein the upper cover opening has substantially the same size and configuration of the upper main body opening; and wherein the lower cover opening has substantially the same size and configuration of the lower main body opening.

* * * * *